US00PP28583P2

(12) United States Plant Patent
Kawaguchi

(10) Patent No.: US PP28,583 P2
(45) Date of Patent: Oct. 31, 2017

(54) ***PODOCARPUS* PLANT NAMED 'SOSA'**

(50) Latin Name: *Podocarpus macrophyllus*
Varietal Denomination: Sosa

(71) Applicant: Kenichi Kawaguchi, Sosa (JP)

(72) Inventor: Kenichi Kawaguchi, Sosa (JP)

( * ) Notice: Subject to any disclaimer, the term of this patent is extended or adjusted under 35 U.S.C. 154(b) by 42 days.

(21) Appl. No.: 14/757,370

(22) Filed: Dec. 22, 2015

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Kawashigeen, Inc. 12th International Flower Expo Tokyo 2015 retrieved on Mar. 30, 2017, retrieved from the Internet at <https://exhibitor.reedexpo.co.jp/IFEX/2015/search/en/detail.phtml?uid=160&eid=4> 1 page.*
Makuhari Messe 12 Internationa Flower Expo 2015, retrieved on Mar. 30, 2017, retrieved from the Internet at <https://www.m-messe.co.jp/en/event/detail/3677> 2 pp.*
Upov Pluto Plant Variety Database 20170309 retrieved on Mar. 13, 2017 for *Podocarpus* 'Sosa', retrieved from the Internet at <www3.wipo.int/pluto/user/en/index.jsp> one page.*

* cited by examiner

*Primary Examiner* — June Hwu
(74) *Attorney, Agent, or Firm* — Penny J. Aguirre

(57) ABSTRACT

A new cultivar of *Podocarpus macrophyllus*, 'Sosa', that is characterized by its new growth tips and leaves that are reddish brown in color in spring and fall, its mature tree trunk cracks in a tortoise shell pattern, its leaves that are short in length and medium in width, its straight trunk with medium tapering, and its limited branching without pruning.

3 Drawing Sheets

Botanical classification: *Podocarpus macrophyllus.*
Variety denomination: 'Sosa'.

CROSS REFERENCE TO A RELATED APPLICATION

This application is related to a plant breeders' rights application filed in Japan on Nov. 16, 2004, application No. 17628. There have been no offers for sale anywhere in the world prior to the filing of this Application and no accessibility to one of ordinary skill in the art could have been derived from printed plant breeder's rights documents.

BACKGROUND OF THE INVENTION

The present invention relates to a new and distinct cultivar of *Podocarpus macrophyllus* and will be referred to hereafter by its cultivar name, 'Sosa'. 'Sosa' is a new cultivar of evergreen shrub grown for use as a landscape shrub.

The new cultivar arose from an ongoing breeding program conducted by the Inventor in Sousa-shi, Chiba, Japan. The new cultivar arose as a naturally occurring branch mutation on an unnamed and unpatented plant of *Podocarpus macrophyllus* growing in a trial field in 2002.

Asexual propagation of the new cultivar was first accomplished by the Inventor using softwood stem cuttings in Sousa-shi, Chiba, Japan in spring of 2002. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sosa' as a unique cultivar of *Podocarpus.*

1. 'Sosa' exhibits new growth tips and leaves that are reddish brown in color in spring and fall.
2. 'Sosa' exhibits mature tree trunk cracks in a tortoise shell pattern.
3. 'Sosa' exhibits leaves that are short in length and medium in width.
4. 'Sosa' exhibits a straight trunk with medium tapering.
5. 'Sosa' exhibits limited branching without pruning.

The parent plant of 'Sosa' differs from 'Sosa' in having green colored growing tips and new foliage. 'Sosa' can be compared to the *Podocarpus macrophyllus* cultivars 'Benikujaku' (not patented) and 'Scarlet bud' (not patented). Both are similar to 'Sosa' in having unique growing tip and new leaf coloration. 'Benikujaku' differs from 'Sosa' in having new growing tips and new foliage that are pinkish red in color. 'Scarlet bud' differs from 'Sosa' in having new growing tips and new foliage that are pinkish in color.

BRIEF DESCRIPTION OF THE DRAWINGS

The accompanying colored photographs illustrate the overall appearance and distinct characteristics of the new cultivar grown in Sosa-shi, Chiba, Japan.

The photograph in FIG. 1 was taken of 5 year-old plants of 'Sosa' as grown in an unheated greenhouse in 21-cm containers.

Figure 1:
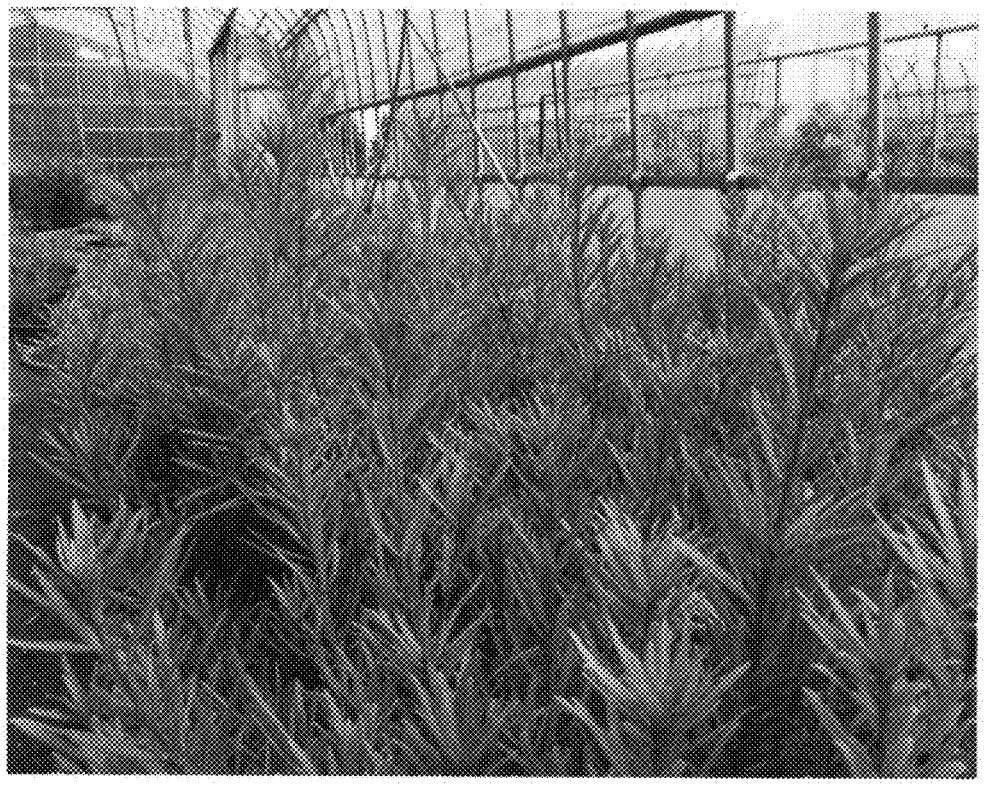
Figure 2:
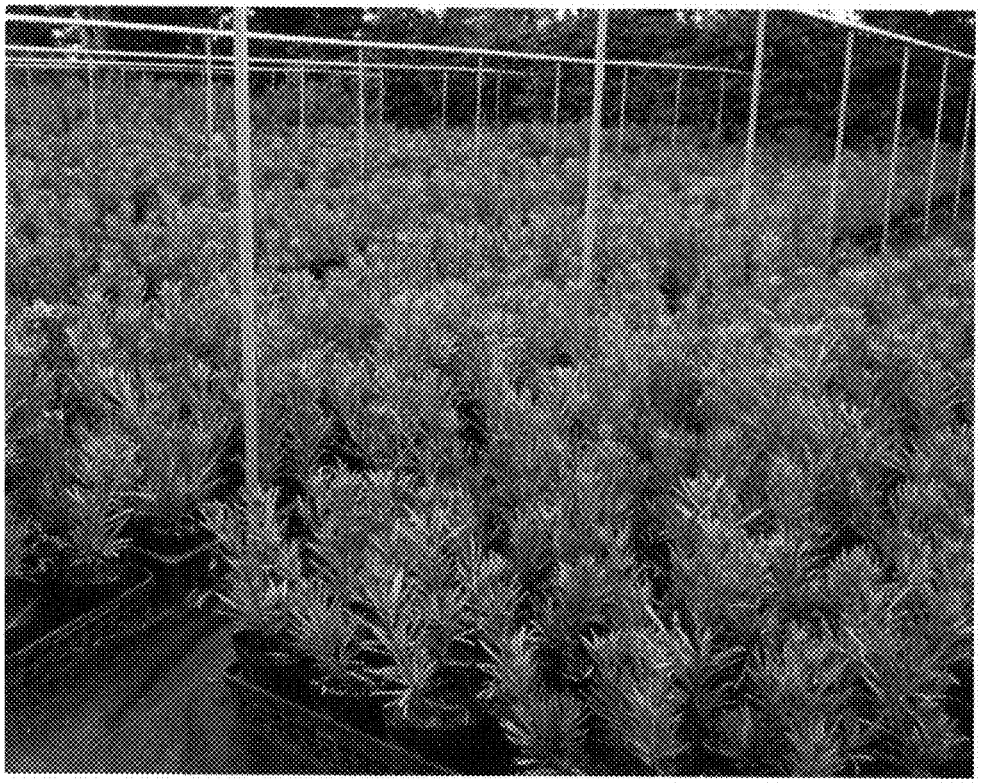

The photograph in FIG. 2 was taken of 4 year-old plants of 'Sosa' as grown outdoors in 18-cm containers.

Figure 3:
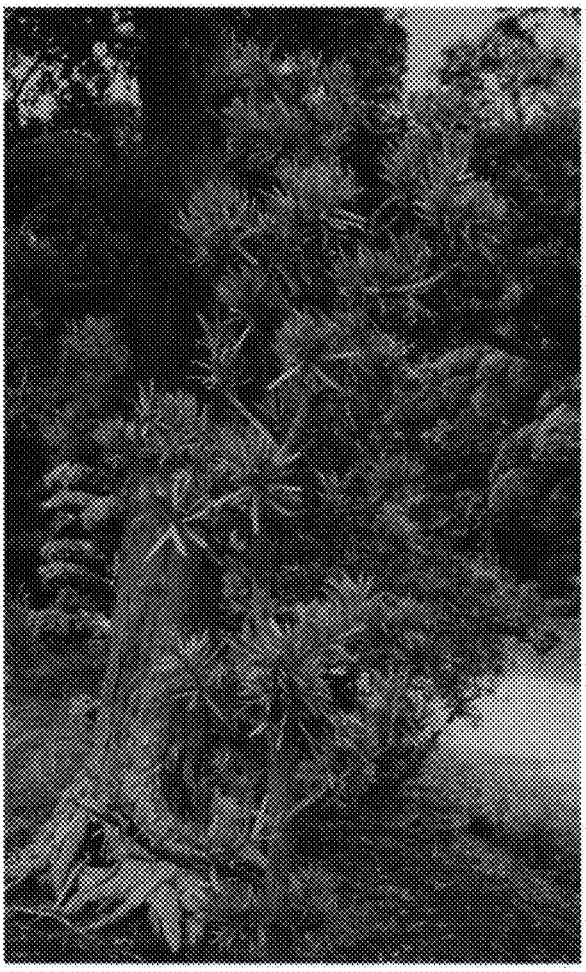

The photograph in FIG. 3 provides a view of a 10 year-old tree as grown in the ground and provides a view of the trunk of 'Sosa'.

All photographs provide a view of the unique growing tip and new foliage coloration that is observed in spring and fall. The colors in the photographs may differ slightly from the color values cited in the detailed botanical description, which accurately describe the colors of the new *Podocarpus*.

DETAILED BOTANICAL DESCRIPTION

The following is a detailed description of 1 year-old plants of the new cultivar as grown outdoors in three-gallon containers in Luxley, Ala. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.

*Plant habit.*—Upright, medium tapering.

*Height and spread.*—Reaches about 50 cm in height and 20 cm in width in a 3-gallon container, mature height in the landscape is 15 to 20 m in height and 5 to 10 m in spread.

*Cold hardiness.*—At least to U.S.D.A. Zones 8b to 11.

*Diseases resistance.*—No susceptibility or resistance has been observed, generally *Podocarpus macrophyllus* is disease free.

*Root description.*—Fibrous.

*Root development.*—Fully root as a young plant in about 6 months.

*Propagation.*—Softwood stem cuttings.

*Growth rate.*—Moderate.

Stem description:

*Shape.*—Round to slightly quadrangular.

*Stem color.*—New growth; 144A with fine ridges of 137A; mature bark; 199A with some areas of 144A showing through the cracks in the bark (as observed on a 10 year-old tree).

*Stem size.*—Main stems; average of 30 cm in length and 6 mm in width, lateral branches; up to 23 cm in length and an average of 3.5 mm in diameter (if present).

*Stem surface.*—New growth; smooth and glabrous with a few fine ridges, maturing growth; patches of smooth bark, mature bark is cracked in a tortoise shell pattern.

*Branching.*—An average of 5 main stems in a 3-gallon container, lateral branches rare if un-pruned (0 to 2).

Foliage description:

*Leaf shape.*—Linear.

*Leaf division.*—Simple.

*Leaf base.*—Attenuate.

*Leaf apex.*—Narrowly acute.

*Leaf fragrance.*—None, but pine scented if crushed.

*Leaf venation.*—Parallel, only midribs are distinguishable, midrib is slightly raised on upper surface, color upper surface 137D, color on lower surface 144B.

*Leaf margins.*—Entire.

*Leaf arrangement.*—Whorled.

*Leaf attachment.*—Sessile.

*Leaf internode length.*—Average of 5 mm in length.

*Leaf surface.*—Glabrous and satiny on upper and lower surface.

*Leaf substance.*—Thick and coriaceous.

*Leaf size.*—An average of 6 cm in length and 7 mm in width.

*Leaf quantity.*—Average of 27 on a branch 12 cm in length.

*Leaf color.*—Growth tips and new leaves in spring and fall; upper surface and lower a blend of 138A, 166B, 166C, and 180B, mature leaves; upper surface 137A, lower surface 137D.

Inflorescence description: Flowers and fruit have not been observed on any plants currently grown.

It is claimed:

1. A new and distinct cultivar of *Podocarpus* plant named 'Sosa' as herein illustrated and described.

* * * * *